US008086277B2

(12) United States Patent
Ganley et al.

(10) Patent No.: US 8,086,277 B2
(45) Date of Patent: Dec. 27, 2011

(54) TRANSMITTER OF WIRELESS MICROPHONE, RECEIVER FOR WIRELESS MICROPHONE, PORTABLE INFORMATION COMMUNICATION DEVICE, AND WIRELESS MICROPHONE COMMUNICATION SYSTEM

(75) Inventors: Richard Ganley, Morden (GB); Tomohisa Tanaka, Hyogo (JP)

(73) Assignee: TOA Corporation, Kobe-shi (JP)

( * ) Notice: Subject to any disclaimer, the term of this patent is extended or adjusted under 35 U.S.C. 154(b) by 760 days.

(21) Appl. No.: 10/564,213

(22) PCT Filed: Jul. 12, 2004

(86) PCT No.: PCT/JP2004/010256
§ 371 (c)(1),
(2), (4) Date: Jul. 17, 2006

(87) PCT Pub. No.: WO2005/006807
PCT Pub. Date: Jan. 20, 2005

(65) Prior Publication Data
US 2007/0037606 A1 Feb. 15, 2007

(30) Foreign Application Priority Data
Jul. 10, 2003 (JP) ................................. 2003-272876

(51) Int. Cl.
*H04M 1/00* (2006.01)
(52) U.S. Cl. ............... 455/569.1; 455/575.1; 455/575.2; 381/92; 381/122
(58) Field of Classification Search ............... 455/569.1, 455/575.1; 381/92, 122
See application file for complete search history.

(56) References Cited

U.S. PATENT DOCUMENTS

| 4,882,773 | A |   | 11/1989 | Maloney |          |
|-----------|---|---|---------|---------|----------|
| 5,003,532 | A |   | 3/1991  | Ashida et al. |   |
| 5,072,442 | A |   | 12/1991 | Todd    |          |
| 5,832,390 | A | * | 11/1998 | Irvin   | 455/569.2 |
| 5,943,649 | A |   | 8/1999  | Motohashi |        |

(Continued)

FOREIGN PATENT DOCUMENTS
EP 0730388 9/1986
(Continued)

OTHER PUBLICATIONS

International Search Report for International Patent Application No. PCT/JP2004/010256 by Japanese Patent Office, dated Oct. 14, 2004 (1 page).
Supplementary Partial European Search Report for International Patent Application No. PCT/JP2004/010256 by European Patent Office, dated Apr. 14, 2009.
Communication issued by European Patent Office in European Application No. EP 04747720.3, dated Sep. 21, 2009.

(Continued)

*Primary Examiner* — Nghi H Ly
(74) *Attorney, Agent, or Firm* — Marshall, Gerstein & Borun LLP

(57) ABSTRACT

A wireless microphone communication system 1 comprises a transmitter 91*b* of a wireless microphone and a receiver 11 for the wireless microphone. The transmitter 91*b* of the wireless microphone includes an infrared interface 91*c*, a control portion 91*d*, and a function control portion 91*e* that controls a function of the wireless microphone. The control portion 91*d* controls the function control portion 91*e* according to information transmitted through the infrared interface 91*c*. The function of the transmitter 91*b* of the wireless microphone is controlled under this control. The receiver 11 of the wireless microphone has the infrared interface 11*c*. The receiver 11 of the wireless microphone sends, through the infrared interface 11*c*, information in the form of the infrared signal to control the function of the transmitter 91*c* of the wireless microphone.

12 Claims, 7 Drawing Sheets

U.S. PATENT DOCUMENTS

| | | | |
|---|---|---|---|
| 6,038,429 A * | 3/2000 | Ahn .............................. | 455/72 |
| 6,057,758 A | 5/2000 | Dempsey et al. | |
| 6,246,325 B1 | 6/2001 | Chittipeddi | |
| 6,317,039 B1 | 11/2001 | Thomason | |
| 6,667,764 B1 | 12/2003 | Wakiyama et al. | |
| 6,987,949 B2 * | 1/2006 | Taniguchi et al. ............. | 455/62 |
| 7,054,625 B2 | 5/2006 | Kawasaki et al. | |
| 2002/0005894 A1 | 1/2002 | Foodman et al. | |
| 2002/0042282 A1 | 4/2002 | Haupt | |
| 2002/0129379 A1 | 9/2002 | Levinson et al. | |
| 2003/0220123 A1 | 11/2003 | Motohashi | |
| 2004/0121819 A1 * | 6/2004 | Vogel .......................... | 455/569.2 |

FOREIGN PATENT DOCUMENTS

| | | |
|---|---|---|
| EP | 1197178 | 4/2002 |
| EP | 1309222 | 5/2003 |
| JP | 61-105997 | 5/1986 |
| JP | 05-183788 | 7/1993 |
| JP | 05-68193 | 9/1993 |
| JP | 10-070472 | 3/1998 |
| JP | 10124790 | 5/1998 |
| JP | 2001045116 | 2/2001 |
| JP | 2001-144645 | 5/2001 |
| JP | 2002-009708 | 1/2002 |
| JP | 2002-156985 | 5/2002 |
| JP | 2003-102074 | 4/2003 |
| JP | 2003-174382 | 6/2003 |

OTHER PUBLICATIONS

Notification of Reasons for Refusal issued in corresponding Japanese Patent Application No. 2005-511607.

International Search Report (ISR) for International Application No. PCT/JP2004/010255 by Japanese Patent Office dated Oct. 21, 2004 (1 page).

Supplementary Partial European Search Report for European Application No. 04747719, dated Mar. 4, 2009.

Non-Final Rejection mailed Mar. 14, 2008 in co-pending U.S. Appl. No. 10/564,255.

Response to Non-Final Office Action submitted on Jul. 14, 2008 in co-pending U.S. Appl. No. 10/564,255.

Final Rejection mailed Oct. 28, 2008 in co-pending U.S. Appl. No. 10/564,255.

Response to Final Office Action submitted on Mar. 26, 2009 in co-pending U.S. Appl. No. 10/564,255.

Non-Final Rejection mailed Sep. 1, 2009 in co-pending U.S. Appl. No. 10/564,255.

Response to Non-Final Office Action submitted on Dec. 17, 2000 in co-pending U.S. Appl. No. 10/564,255.

Final Rejection mailed Mar. 16, 2010 in co-pending U.S. Appl. No. 10/564,255.

Response to Non-Final Office Action submitted on Jul. 8, 2010 in co-pending U.S. Appl. No. 10/564,255.

* cited by examiner

TRANSMITTER OF WIRELESS MICROPHONE, RECEIVER FOR WIRELESS MICROPHONE, PORTABLE INFORMATION COMMUNICATION DEVICE, AND WIRELESS MICROPHONE COMMUNICATION SYSTEM

CROSS-REFERENCE TO RELATED APPLICATION

The present application claims the benefit of priority of International Patent Application No. PCT/JP2004/010256 filed on Jul. 12, 2004, which application claims priority of Japanese Patent Application No. 2003-272876 filed Jul. 10, 2003. The entire text of the priority application is incorporated herein by reference in its entirety.

TECHNICAL FIELD

The present invention relates to a wireless microphone communication system, and a transmitter, a receiver, and a portable information communication device that configure the system. More particularly, the present invention relates to a system configured to communicate information between two devices of the transmitter, the receiver, and the portable information communication device.

BACKGROUND ART

A wireless microphone has various functions, for example, a function for controlling an output level of a radio wave and a display function. An operation portion for controlling these functions is provided in the wireless microphone. A user of the wireless microphone operates the operation portion to thereby control the functions of the wireless microphone.

For example, in a case where a play is performed on a stage and a performer is carrying and using the wireless microphone, the performer has difficulty in operating the operation portion of the wireless microphone and may in many cases erroneously operate the operation portion.

DISCLOSURE OF THE INVENTION

Under the circumstances, the present invention has been developed. An object of the present invention is to provide a wireless microphone communication system, a transmitter, a receiver, and a portable information communication device that enable functions of a wireless microphone to be controlled without depending on a user's operation.

In order to achieve the above mentioned object, a transmitter of a wireless microphone of the present invention comprises an infrared interface; a control portion; a storage portion; and a function control portion that controls a function of the wireless microphone; wherein the transmitter has one of or both of an information transmission function and an information reception function; the information transmission function is to transmit, through the infrared interface, information regarding the wireless microphone which is stored in the storage portion; and the information reception function is to receive the information regarding the wireless microphone through the infrared interface and to control the function control portion by the control portion according to the information regarding the wireless microphone to thereby control the function of the wireless microphone.

In order to achieve the above mentioned object, a receiver for a wireless microphone of the present invention comprises an infrared interface; wherein the receiver has one of or both of an information transmission function and an information reception function; the information transmission function is to transmit, through the infrared interface, information regarding the wireless microphone; and the information reception function is to receive, through the infrared interface, the information regarding the wireless microphone.

In order to achieve the above mentioned object, a portable information communication device comprises an infrared interface; and a storage portion; wherein the portable information communication device has one of or both of an information transmission function and an information reception function; the information transmission function is to transmit, through the infrared interface, information regarding the wireless microphone which is stored in the storage portion; and the information reception function is to receive, through the infrared interface, the information regarding the wireless microphone and to store the information in the storage portion.

In order to achieve the above mentioned object, a wireless microphone communication system of the present invention comprises an infrared signal transmitting device; and an infrared signal receiving device; wherein the infrared signal transmitting device is a receiver for a wireless microphone that has at least an information transmission function, or a portable information communication device that has at least the information transmission function; wherein the infrared signal receiving device is a transmitter of the wireless microphone that has at least an information reception function, or a portable information communication device that has at least the information reception function; wherein the infrared signal transmitting device is configured to transmit, using the information transmission function, information regarding the wireless microphone through the infrared interface; and wherein the infrared signal receiving device is configured to receive, using the information reception function, the information regarding the wireless microphone that is transmitted from the infrared signal transmitting device, through the infrared interface.

In accordance with the transmitter, the receiver, the portable information communication device or the wireless microphone communication system configured as described above, the function of the wireless microphone is controlled by externally sending an infrared signal. This eliminates a need for a user of the wireless microphone to operate the operation portion. As a result, erroneous operation performed by the user is avoided.

In the wireless microphone communication system, the information regarding the wireless microphone may be command information, and the command information may be to command the transmitter of the wireless microphone to control a function of the wireless microphone.

In the wireless microphone communication system, the command information may be information regarding an amplitude frequency characteristic of a sound signal, and the command information may be to command the transmitter of the wireless microphone to control the amplitude frequency characteristic of the sound signal.

In the wireless microphone communication system, the command information may be information regarding a gain of a sound signal, and the command information may be to command the transmitter of the wireless microphone to control a gain given to the sound signal.

In the wireless microphone communication system, the command information may be information regarding a frequency of a carrier wave, and the command information may be to command the transmitter of the wireless microphone to control the frequency of the carrier wave.

In the wireless microphone communication system, the command information may be information regarding an output level of a carrier wave, and the command information may be to command the transmitter of the wireless microphone to control the output level of the carrier wave.

In the wireless microphone communication system, the command information may be information regarding whether or not to permit a setting condition of the transmitter to be changed, and the command information may be to command the transmitter of the wireless microphone to enable or disable an operation portion of the transmitter of the wireless microphone to change the setting condition.

In the wireless microphone communication system, the command information may be information regarding deviation, and the command information may be to command the transmitter of the wireless microphone to control the deviation.

In the wireless microphone communication system, the command information may be information regarding a pilot tone, and the command information may be to command the transmitter of the wireless microphone to start or stop transmission of the pilot tone.

In the wireless microphone communication system, the command information may be information regarding a display, and the command information may be to command the transmitter of the wireless microphone to cause the display into an operating state or a non-operating state.

In the wireless microphone communication system, the command information may be information regarding a compander, and the command information may be to command the transmitter of the wireless microphone to control a characteristic of the compander.

In the wireless microphone communication system, the command information may be information regarding a mute function, and the command information may be to command the transmitter of the wireless microphone to cause the mute function into an operating state or a non-operating state.

In the wireless microphone communication system, the information regarding the wireless microphone may be attribute information, and the attribute information may be to inform the infrared signal receiving device of attribute of the transmitter of the wireless microphone.

In the wireless microphone communication system, the attribute information may be information regarding a type of a battery used in the transmitter of the wireless microphone.

In the wireless microphone communication system, the attribute information may be information regarding a number or a name assigned to the transmitter of the wireless microphone.

In order to achieve the above mentioned object, another wireless microphone communication system of the present invention comprises a first infrared signal transmitting and receiving device; and a second infrared signal transmitting and receiving device; wherein the first infrared signal transmitting and receiving device is a receiver for a wireless microphone that has an information transmission function and an information reception function, or a portable information communication device that has the information transmission function and the information reception function; wherein the second infrared signal transmitting and receiving device is a transmitter of the wireless microphone that has the information transmission function and the information reception function, or a portable information communication device that has the information transmission function and the information reception function; wherein the first infrared signal transmitting and receiving device is configured to transmit, using the information transmission function, reply request information regarding the wireless microphone through the infrared interface; wherein the second infrared signal transmitting and receiving device is configured to receive, using the information reception function, a reply request signal that is transmitted from the first infrared signal transmitting and receiving device, through the infrared interface, and to transmit, using the information transmission function, reply information through the infrared interface in response to a request of the reply request signal; and wherein first infrared signal transmitting and receiving device is configured to, using the information reception function, receive the reply information transmitted from the second infrared signal transmitting and receiving device through the infrared interface.

In accordance with the wireless microphone communication system configured as described above, also, the function of the wireless microphone may be controlled by externally sending an infrared signal. This eliminates a need for a user of the wireless microphone to operate the operation portion. As a result, erroneous operation performed by the user is avoided In the wireless microphone communication system, the reply request information may be to request the transmitter of the wireless microphone to inform a setting condition of the transmitter; and the reply information is information regarding the setting condition of the transmitter of the wireless microphone.

In order to achieve the above mentioned object, another transmitter of a wireless microphone of the present invention comprises an infrared interface; a control portion; and a function control portion that controls a function of the wireless microphone; wherein the control portion is configured to control the function control portion according to information sent through the infrared interface to thereby control the function of the wireless microphone.

In order to achieve the above mentioned object, another receiver for a wireless microphone of the present invention comprise an infrared interface; wherein the receiver is configured to transmit, through the infrared interface, information in a form of an infrared signal to control a function of a transmitter of the wireless microphone.

In order to achieve the above mentioned object, another portable information communication device comprises an infrared interface; wherein the portable information communication device is configured to transmit, through the infrared interface, information in a form of an infrared signal to control a function of a transmitter of the wireless microphone.

In order to achieve the above mentioned object, another wireless microphone communication system of the present invention comprises an infrared signal transmitting device; and an infrared signal receiving device; wherein the infrared signal transmitting device is a receiver for a wireless microphone, or a portable information communication device; and wherein the infrared signal receiving device is a transmitter of the wireless microphone.

In the wireless microphone communication system, the information in the form of the infrared signal may be command information; and the transmitter of the wireless microphone may be configured to control a function of the wireless microphone according to the command information, upon receiving the command information.

These objects as well as other objects, features and advantages of the invention will become more apparent to those skilled in the art from the following description with reference to the accompanying drawings.

BEST MODE FOR CARRYING OUT THE INVENTION

Embodiments of the present invention will be described with reference to the drawings.

Figure 1:
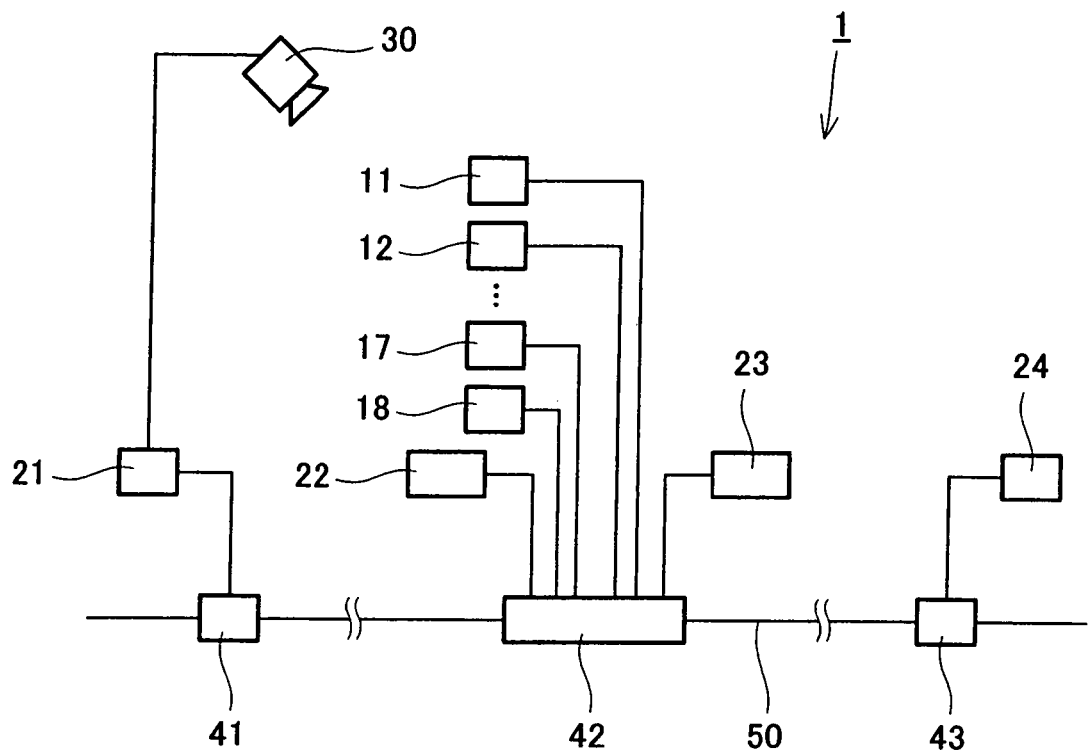
FIG. 1 is a block diagram of a wireless microphone communication system.

FIG. 1 is a block diagram of a wireless microphone communication system 1 according to an embodiment of the present invention.

The wireless microphone communication system 1 is installed for a performance on a stage.

The wireless microphone communication system in FIG. 1 comprises receivers 11, 12, . . . , 17 and 18 that respectively receive radio waves from transmitters of the wireless microphones, computers 21, 22, 23, and 24 which are control devices, and a television camera 30.

The receivers 11, 12, . . . , 17 and 18 and the computers 21, 22, 23, and 24 have LAN interfaces. The receivers 11 to 18 and the computers 21 to 24 are coupled to Ethernet 50 through HUB 41, 42, and 43, thus entirely configuring LAN.

The television camera 30 is coupled to the computer 21.

The computer 24 is installed at a position from which the computer 24 is able to observe the entire stage. At that position, there is installed a mixing console for controlling entire electric acoustic equipment (loudspeaker) for emitting a loud sound wave of the voice that is received by the wireless microphone. An operator A stands by near the computer 24.

The receivers 11 to 18 and the computer 22 are installed on a wing of the stage. An operator B stands by near the receivers 11 to 18 and the computer 22.

Figure 2:
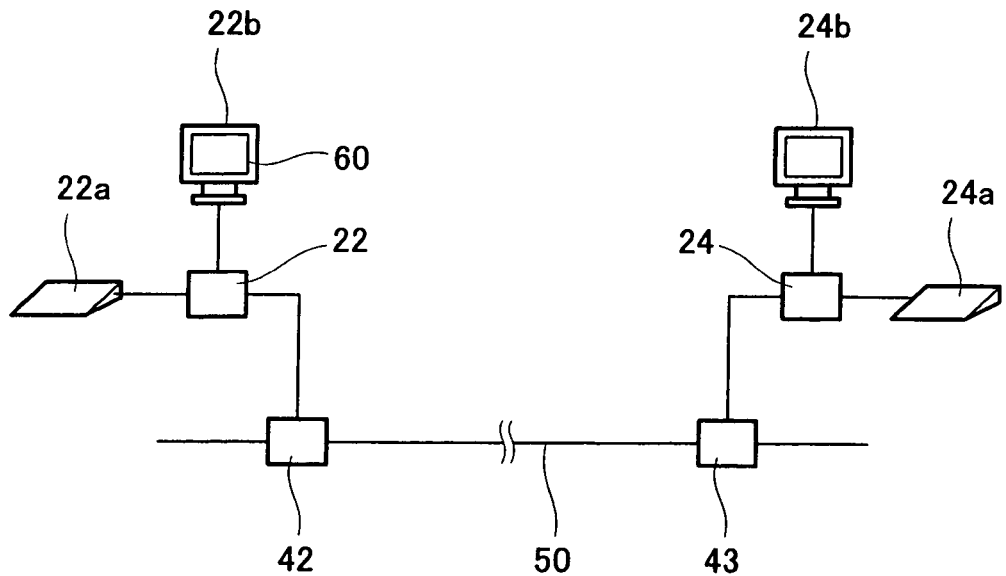
FIG. 2 is a block diagram showing computers and peripheral devices coupled to the computers.

FIG. 2 is a block diagram showing the computers 22 and 24 and peripheral devices coupled to the computers 22 and 24. Although not shown in FIG. 1, a key board 22a which is an input device and a display device 22b are coupled to the computer 22. A key board 24a which is an input device and a display device 24b are coupled to the computer 24. Although not shown in FIG. 2, key boards and display devices are coupled to the computers 21 and 23 in the same manner.

The computers 21 to 24 receive information from the receivers 11 to 18 through the LAN. The information from the receivers 11 to 18 includes an RF level (receiving field intensity), an audio output level (VU level), etc. Information indicating battery powers of the wireless microphones are output from the wireless microphones corresponding to the receivers 11 to 18, and the computers 21 to 24 receive information indicating the battery powers from the receivers 11 to 18.

An application program E to which these information are input runs on the computers 21 to 24. The same application program E runs on the computers 21 to 24.

Character string information input from the key board, as well as the information from the receivers 11 to 18, are input to the application program E. The application program E causes the corresponding display device to display one window.

Figure 3:
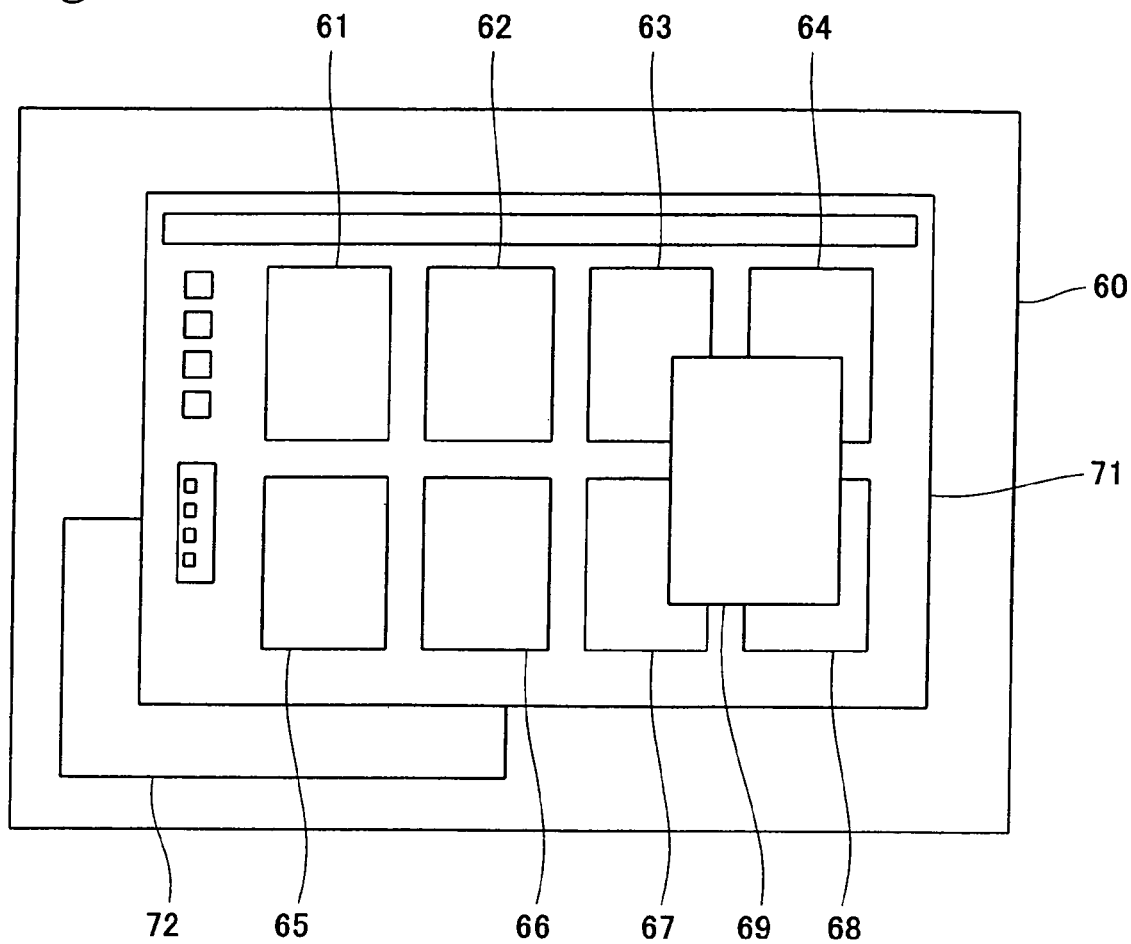
FIG. 3 is a diagram of a display region of a display device.

FIG. 3 shows a display region 60 of the display device 22b. On the display region 60, a window 71 associated with the application program E and a window 72 associated with another application program F are displayed. The same window as the window 71 of the display device 22b is displayed on each of display devices coupled to the computers other than the computer 22.

The window 71 has receiver regions 61 to 68 that display the information from the receivers 11 to 18 and a character string region 69 that displays character strings.

Figure 4:
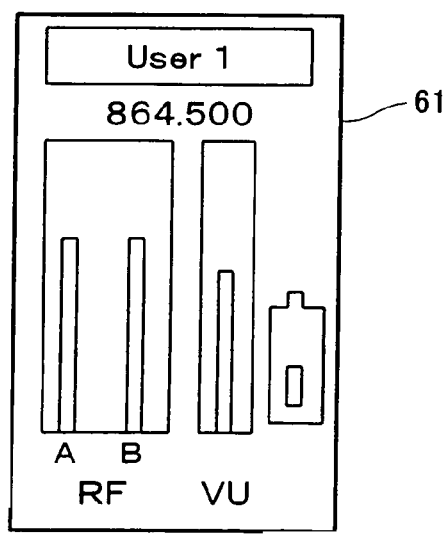
FIG. 4 is a diagram of a receiver region.

FIG. 4 shows the receiver region 61. The information from the receiver 11 is displayed on the receiver region 61. The RF level is displayed on the receiver region 61. The RF level is displayed as "A" and "B". This is because the radio wave from the wireless microphone is received in diversity format. That is, the RF levels regarding antenna A and antenna B are separately displayed.

The battery power is displayed on a right lower region of the receiver region 61. The battery power means the battery power of the wireless microphone corresponding to the receiver 11.

The VU level is displayed on the receiver region 61.

"User 1" displayed on the display region 61 is a number by which the receiver (or the corresponding wireless microphone) is identified.

A desired name may be set as this number by the user.

"864.500" displayed on the receiver region 61 indicates a frequency of the radio wave used by the receiver (or corresponding wireless microphone) by "MHz."

Likewise, the RF level, the battery power, the VU level, the number by which the receiver (or corresponding wireless microphone) is identified, and the frequency are displayed on each of the receiver regions 62 to 68 other than the receiver region 61.

Figure 5:
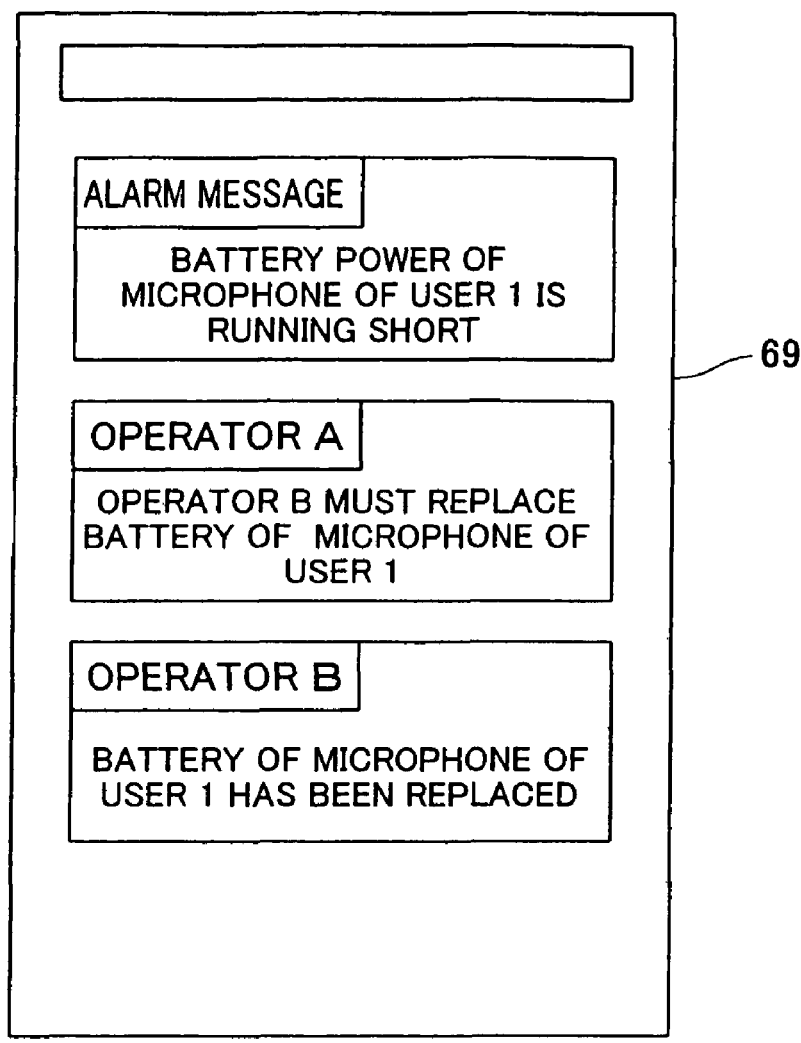
FIG. 5 is a diagram of a character string region.

FIG. 5 shows the character string region 69 on the window 71. On the character string region 69, an alarm message, a character string entered from the keyboard 24a by the operator A, and a character string entered from the keyboard 22a by the operator B are displayed.

These character strings are displayed in the following order. First, the computers 21 to 24 recognize the states of the batteries (battery powers) of the wireless microphones corresponding to the receives 11 to 18 through the LAN. When the computer (application program E) recognizes that the battery power is a predetermined threshold or less, the character string region 69 containing the alarm message is displayed on the window 71. As the alarm message, a message stating that "BATTERY POWER OF THE MICROPHONE OF USER 1 IS RUNNING SHORT" is displayed on the character string region 69.

The operator A near the computer 24 reads the alarm message displayed on the display device 24b, and enters a character string "THE OPERATOR B MUST REPLACE THE BATTERY OF THE MICROPHONE OF THE USER 1" from the key board 24a in order to instruct the operator B to replace the battery. So, this character string is displayed on the character string region 69 of the display device 24b. This character string is communicated to the computers 21 to 23 through the LAN, and is displayed on the character string region 69 of the display device of each of the computers 21 to 23.

Since the character string is displayed on the character string region 69 of the display device 22b, the operator B recognizes the instruction for replacing the battery from the operator A. In accordance with the instruction of this character string, the operator B replaces the battery of the microphone of the User 1. Then, the operator B enters a character string "THE BATTERY OF THE MICROPHONE OF THE USER 1 HAS BEEN REPLACED" from the keyboard 22*a*. So, this character string is displayed on the character string region 69 of the display device 22*b*. This character string is communicated to the computers 21, 23, and 24 through the LAN, and is displayed on the character string region. 69 of the display device of each of the computers 21, 23, and 24.

The operator A reads this character string on the display device 24*b*, and confirms that the operator B has replaced the battery as instructed by the operator A.

In the manner described above, the same content is displayed on the display device 22*b* and the display device 24*b*. Thus, the operator A and the operator B are able to share information indicating the state of the wireless microphone communication system 1.

Thus, the same application program E runs on the respective computers 21 to 24. The computers 21 to 24 receive the information from the receivers 11 to 18 and the character string information from the computers 22 and 24 through the LAN. Therefore, the same content is displayed on the display devices coupled to the computers 21 to 24.

If a computer is installed at a location remote from the receivers 11 to 18, the operators are able to recognize the states of the receivers 11 to 18 by that computer so long as that computer is coupled to the receivers 11 to 18 through the LAN.

As mentioned above, the wireless microphone communication system 1 comprises the television camera 30 which is coupled onto the LAN. Image information from the television camera 30 may be displayed on the display devices 22*b* and 24*b* along with the information from the receivers 11 to 28. Alternatively, the image information from the television camera 30 may be stored in storage portions of the computers 22 and 24. In a further alternative, the image information from the television camera 30 and information based on the information from the receivers 11 to 18 may be stored in the storage portions of the computers 22 and 24.

The alarm message includes various messages in addition to the battery power. For example, if the RF level continues to be a predetermined value or less for a predetermined time period or more, then an alarm message stating this may be displayed. That is, it is necessary to display an alarm message stating abnormality or failure of the wireless microphone communication system 1, upon detecting them.

While each operator enters the character string from the key board to communicate with another operator, he/she may select a desired message from messages prepared in advance to display the desired message on the character string region 69.

In addition to the character strings which are entered or selected, some information entered with respect to a computer by an operator may be displayed on display devices coupled to another computers as well as a display device coupled to that computer. This makes it possible that plural operators share that information. As a result, the operators are able to communicate with each other correctly. For example, a marking or the like made on a display region of a display device by an operator may be displayed on display devices of all computers.

The character string region on which the alarm message or the character string entered by the operator are displayed may appear on the display device 22*b* as being associated with a receiver region (or transmitter region) on which an abnormal state of a receiver in which abnormality has occurred (or the corresponding transmitter) is displayed.

For example, the plural receiver regions may have different colors. By the color of the receiver region corresponding to the receiver associated with the information of the character string, the character string region 69 of this character string may be displayed on the display device 22. To be specific, in FIG. 3, assuming that the receiver regions 61 to 68 have different colors, the color of the receiver region 61 is blue, and information of the character string of the character string region 69 indicates abnormality of the receiver 11, the character string region 69 may be represented by blue on the display device 22*b*.

Furthermore, the character string region 69 on which the alarm message or the character string entered by the operator are displayed may be configured to appear near the receiver region (or transmitter region) on which the abnormal state of the receiver in which abnormality has occurred (or the corresponding transmitter) is displayed. For example, the character string region on which the alarm message or the character string entered by the operator are displayed may be configured to appear near the receiver region (or transmitter region) on which the abnormal state of the receiver in which abnormality has occurred is displayed, by pop up display. With such a configuration, each operator is able to recognize the abnormal state of the receiver directly.

The receiver region (or the transmitter region) on which the abnormal state of the receiver in which abnormality has occurred (or the corresponding transmitter) is displayed may be displayed in a display configuration different from those of receiver regions (or transmitter regions) of another receivers, for example, with a different color. Furthermore, the messages may be displayed by different colors according to the kind. This makes it easy that the operator visually checks the message. Furthermore, a destination to which a message is directed may be selected. By selecting a particular destination and sending the message to it, conflict of the message is avoided.

Subsequently, a method of detecting a dead point on the stage by the wireless microphone communication system 1 will be described.

Figure 6:
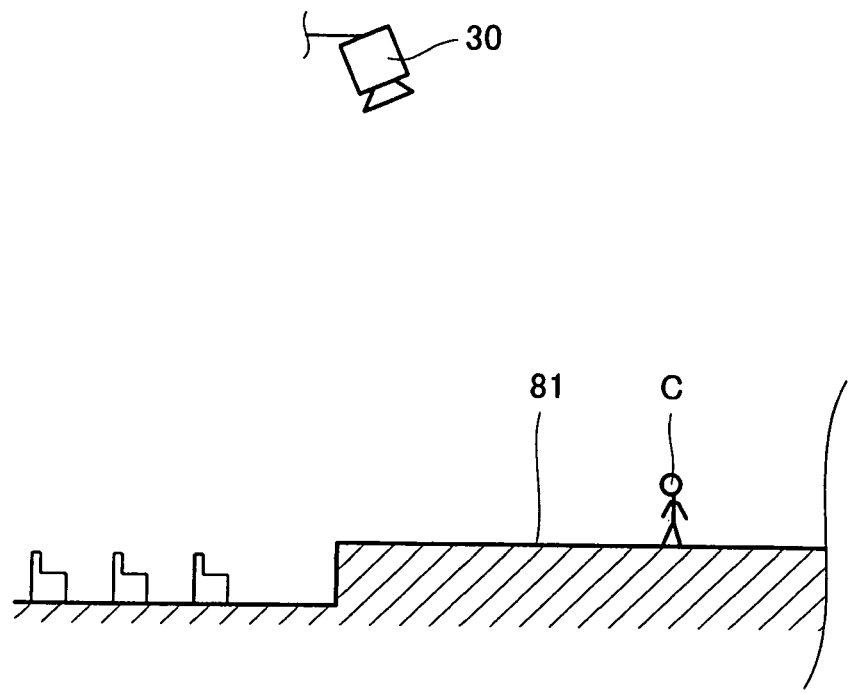
FIG. 6 is a longitudinal sectional view of a stage on which a television camera is installed.

FIG. 6 is a longitudinal sectional view of a stage 81 on which the television camera 30 is installed. As described previously, the wireless microphone communication system 1 is equipped with the television camera 30. The television camera 30 is installed above the stage 81 to take an image of the entire stage 81 from above. FIG. 6 illustrates an operator C on the stage 81. The operator C carries a wireless microphone.

Figure 7:
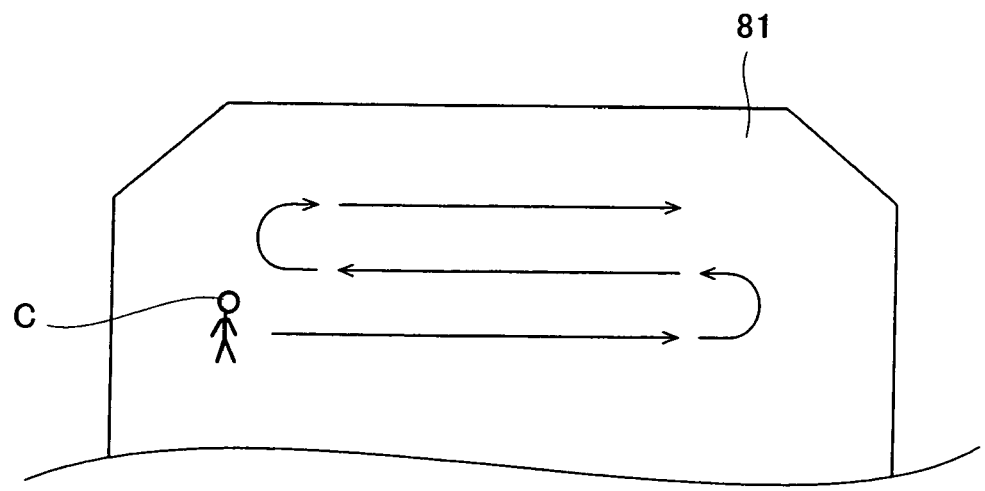
FIG. 7 is a plan view of the stage.

FIG. 7 is a plan view of the stage 81. The operator C appears on the stage 81. The operator C moves along a path indicated by an arrow in FIG. 7. In this way, the operator C walks around on the stage 81.

A radio wave from the wireless microphone carried by the operator C is received by the corresponding receiver. From this receiver, information regarding the RF level is sent to the computer 21 through the LAN.

Figure 8:
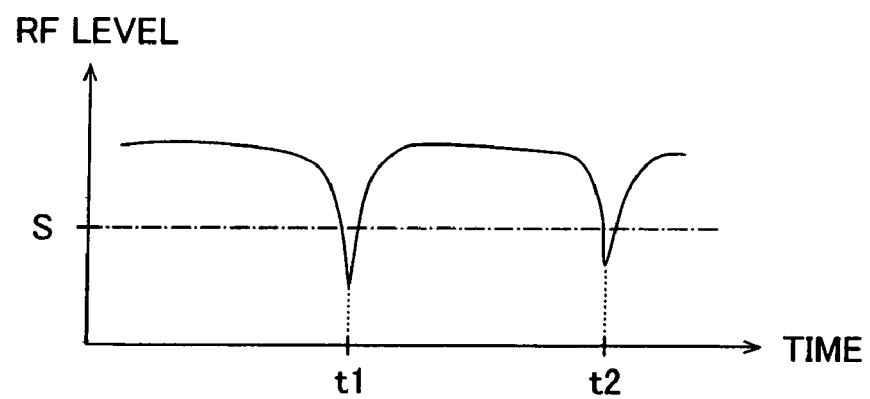
FIG. 8 is a view showing a RF level that varies with time.

FIG. 8 is a view showing the RF level that varies with time. The computer 21 continuously receives the information of the RF level on a time axis and determines whether or not the RF level is not higher than a predetermined level (threshold level). In FIG. 8, "S" indicates the predetermined level (threshold level). Turning to FIG. 8, the RF level is not higher than the level S at time t1 and time t2. The diagram illustrated in FIG. 8 may be displayed on the display device coupled to the computer 21.

The computer 21 receives the information of the RF level and image information from the television camera 30. When determining that the RF level is not higher than the predetermined level (threshold level), the computer 21 stores the image information at that time in a storage means.

Figure 9:
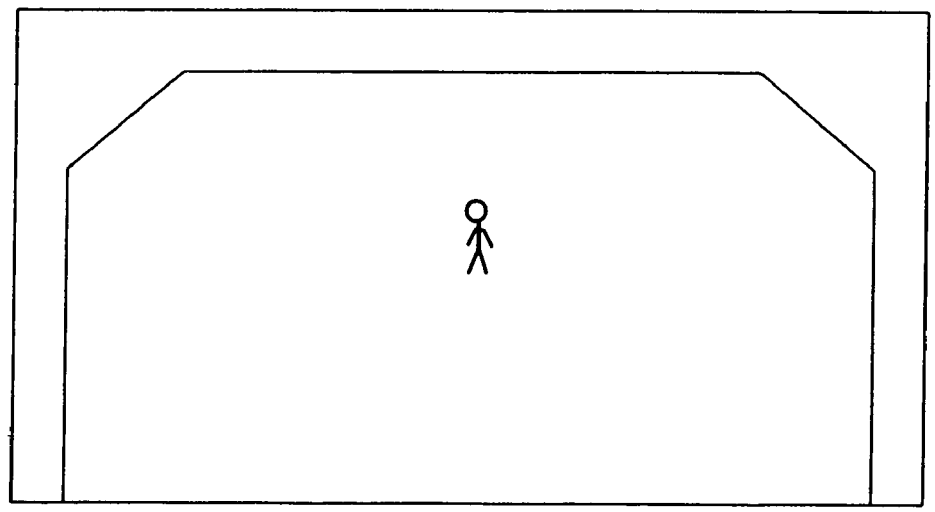
FIG. 9 is a view showing an image at time t1 which the computer receives from the television camera.

FIG. 9 illustrates an image at time t1 which is received by the computer 21 from the television camera 30. Since the RF level is not higher than the predetermined level (threshold level) at time t1, the image (image in FIG. 9) is stored in the storage means. Likewise, an image at time t2 is stored in the storage means.

It is highly probable that, when the RF level is not higher than the predetermined level, a position of the operator C at that point of time is a dead point of the wireless microphone. By checking the stored images later, the position of the dead point on the stage is recognized.

In accordance with the detection method of the dead point, the dead point is accurately detected only by one operator.

In this embodiment, an operation portion of the computer 21 functions as a control means and a memory of the computer 21 functions as the storage means. The operation portion of the computer 21 which is the control means determines whether or not the RF level is not higher than the predetermined level, and when determining that the detected RF level is not higher than the predetermined level, the image information from the television camera 30 at that point of time is stored in the memory of the computer 21 which is the storage means.

The computer 21 includes a time measuring means. Time information from the time measuring means may be stored in the memory together with the image information from the television camera 30.

In the above illustrated example, the television camera 30 is coupled to the computer 21. Alternatively, the television camera 30 may have a communication function. In that case, the television camera 30 may be directly coupled to the LAN without the computer 21.

Figure 10:
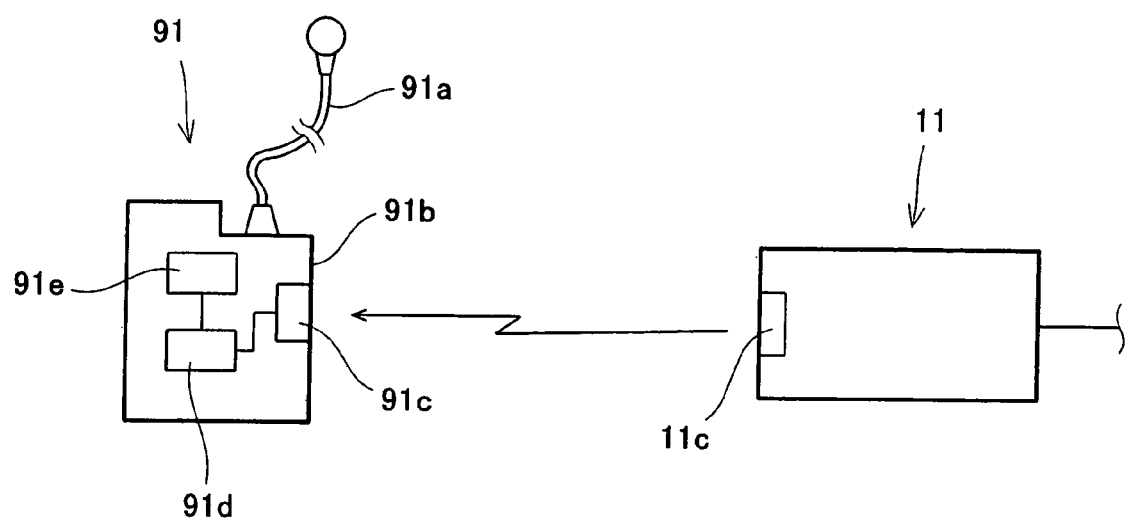
FIG. 10 is a block diagram schematically showing a configuration of a wireless microphone and a receiver.

FIG. 10 is a block diagram schematically showing a configuration of the wireless microphone 91 and the receiver 11. The wireless microphone 91 corresponds to the receiver 11. A radio wave from the wireless microphone 91 is received by the receiver 11. The wireless microphone 91 is a lavaliere type wireless microphone and includes a sound receiving portion 91a and a transmitter 91b. The transmitter 91b of the wireless microphone 91 includes an infrared interface 91c, a control portion 91d, a function control portion 91e, and a storage portion (not shown). The function control portion 91e serves to control respective functions of the wireless microphone 91, for example, a frequency and a gain of the wireless microphone 91. Various information regarding setting conditions of the wireless microphone 91 are stored in the storage portion.

The wireless microphone 91 has the infrared interface 91c. The receiver 11 corresponding to the wireless microphone 91 has an infrared interface 11c. Information is output from the infrared interface 11c of the receiver 11 in the form of an infrared signal. This information is information that has been directed from any one of the computers 21 to 24 to the receiver 11. The information from the infrared interface 11c of the receiver 11 is received by the infrared interface 91c of the wireless microphone 91. This information is sent to the control portion 91d, which controls the function control portion 91e according to this information. The transmitter 91b performs various operations according to the information from the infrared interface 11c of the receiver 11. Information is output from the infrared interface 91c of the wireless microphone 91 in the form of the infrared signal and is received by the infrared interface 11c of the receiver 11. That is, the transmitter 91b of the wireless microphone 91 and the receiver 11 have a function to transmit the information in the form of the infrared signal and a function to receive the information in the form of the infrared signal. The infrared signal is used to transmit the information, and does not interfere with the radio wave of the wireless microphone 91. In other words, this signal (infrared signal) does not negatively affect the sound signal of the wireless microphone 91 as a noise.

As described above, the transmitter 91b performs various operations according to the type of the information from the infrared interface 11c of the receiver 11. Hereinafter, various information from the infrared interface 11c of the receiver 11 and how the transmitter 91b operates according to this information will be described. The transmitter 91b performs various operations under the condition in which the control portion 91d controls the function control portion 91e.

The information from the infrared interface 11c of the receiver 11 includes command information, attribute information, and reply request information.

When the information from the infrared interface 11c of the receiver 11 is the command information, the transmitter 91b controls the function of the wireless microphone 91 according to the command information, upon receiving the command information. The command information includes various information.

When the command information is information regarding an amplitude frequency characteristic of a sound signal, the transmitter 91b controls the amplitude frequency characteristic of the sound signal according to the command information, upon receiving the command information. Thereby, quality of the sound signal which is output from the wireless microphone 91 is controlled.

When the command information is information regarding a gain of the sound signal of the transmitter 91b, the transmitter 91b controls the gain given to the sound signal according to the command signal, upon receiving the command information. Thereby, the level of the sound signal which is output from the wireless microphone 91 is controlled.

When the command information is information regarding a frequency of a carrier wave of the transmitter 91b, the transmitter 91b controls the frequency of the carrier wave according to the command information, upon receiving the command information. That is, the frequency of the radio wave from the wireless microphone 91 is changed.

When the command information is information regarding an output level of the carrier wave of the transmitter 91b, the transmitter 91b controls the output level of the carrier wave according to the command information, upon receiving the command information. The radio wave with a higher output level is sent to a remote place.

When the command information is information regarding whether or not to change the setting conditions of the transmitter 91b, the transmitter 91b enables or disables the setting conditions to be changed by the operation portion of the transmitter 91b according to the command information, upon receiving the command information. That is, the user of the wireless microphone 91 is allowed or not allowed to operate the operation portion to change the setting conditions of the wireless microphone 91. The user of the wireless microphone 91 is disabled to change the setting conditions in order to inhibit the user from erroneously operating the wireless microphone 91.

When the command information is information regarding deviation of the transmitter 91b, the transmitter 91b controls deviation according to the command information, upon receiving the command information. The deviation refers to a frequency bias of a modulated wave.

When the command information is information regarding a pilot tone of the transmitter 91b, the transmitter 91b starts or stops transmission of the pilot tone according to the command information, upon receiving the command information. The pilot tone refers to a signal used to establish symbol synchronization.

When the command information is information regarding the display of the transmitter 91b, the transmitter 91b causes the display to be turned to an operating state or a non-operating state according to the command information, upon receiving the command information. The transmitter 91b is equipped with the display which displays the setting conditions of the transmitter 91b. The term "the display is turned to the operating state" means that the display is turned to ON-state. The term "the display is turned to the non-operating state" means that the display is turned to OFF-state.

When the command information is information regarding a compander of the transmitter 91b, the transmitter 91b controls a characteristic of the compander according to the command information, upon receiving the command information. That is, the transmitter 91b controls a configuration of the compander. The compander is a device that expands and compresses the sound signal. The compander is used to enlarge a dynamic range and reduce a noise.

When the command information is information regarding a mute function of the transmitter 91b, the transmitter 91b causes the mute function to be turned to the operating state or the non-operating state according to the command information, upon receiving the command information. The term "mute function" refers to a function to mute the sound signal.

When the information from the infrared interface 11c of the receiver 11 is attribute information of the transmitter 91b, the transmitter 91b writes the attribute information in an internal storage portion, upon receiving the attribute information. The attribute information includes various information.

When the attribute information is information regarding the type of the battery to be used by the transmitter 91b, the transmitter 91b writes the type according to the received attribute information in the internal storage portion. Thus, the transmitter 91b is able to recognize the type of the battery built in the wireless microphone 91. The reason why the transmitter 91b is informed of the type of the battery is that the relationship between the battery voltage and the battery power varies according to the type of the battery. The remaining operating time of the wireless microphone is determined chiefly by the battery power of the battery. The transmitter 91b measures the battery voltage and displays the remaining operating time of the wireless microphone 91 on the display. The transmitter 91b is caused to recognize the type of the battery in order to display the correct operating time.

When the attribute information is information regarding a number or a name assigned to the transmitter 91b, the transmitter 91b writes the number or the name according to the received attribute information in the internal storage portion. Thereby, the transmitter 91b is able to recognize the number or the name assigned to the transmitter 91b and to display the number or the name on the display. The user of the wireless microphone 91 is able to recognize the number or the name assigned to the transmitter 91b of the wireless microphone 91b used by the user according to the content displayed on the display.

The infrared interface 91c of the wireless microphone 91 and the infrared interface 11c of the receiver 11 have a two-way communication function. The transmitter 91b sends reply information to the receiver 11 in order to inform the receiver 11 that the wireless microphone 91 has received the signal or the transmitter 91b performed control correctly according to the information from the receiver 11. In this manner, correct communication is carried out.

The reply information is output from the infrared interface 91c of the transmitter 91b of the wireless microphone 91 when a signal of the reply request information is output from the infrared interface 11c of the receiver 11.

When the signal of the reply request information is output from the interface 11c of the receiver 11 and the transmitter 91b receives the reply request information, the transmitter 91b sends the reply information to the receiver 11 in the form of the infrared signal according to the reply request information.

The reply request information includes various information. For example, when the reply request information is information to request the transmitter 91b to send the setting conditions of the transmitter 91b to the receiver 11, the transmitter 91b sends information regarding the setting conditions as the reply information according to the reply request information, upon receiving the reply request information. The information regarding the setting conditions includes an amplitude frequency characteristic of the sound signal of the transmitter 91b or information regarding the gain given to the sound signal of the transmitter 91b. These information are stored in the storage portion of the transmitter 91b of the wireless microphone 91. When the information of all the setting conditions of the transmitter 91b have been sent to the receiver 11, another transmitters may be configured to change setting conditions into those identical to the setting conditions of the transmitter 91b.

Figure 11:
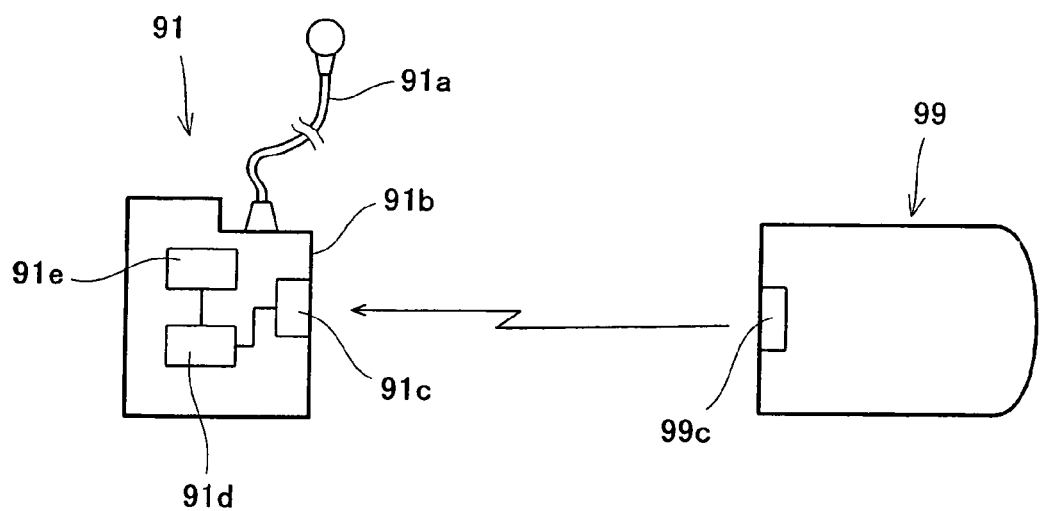
FIG. 11 is a block diagram schematically showing a configuration of the wireless microphone and a personal digital assistance (PDA)

FIG. 11 is a block diagram schematically showing a configuration of the wireless microphone 91 and a personal digital assistant (PDA) 99. As described previously, the function of the wireless microphone 9 is controlled according to the information in the form of the infrared signal. This information need not be output from the receiver 11. For example, this information may be output from the personal digital assistant (PDA) 99. The personal digital assistance (PDA) 99 in FIG. 11 includes an infrared interface 99c from which the information is output in the form of the infrared signal. This information is received by the infrared interface 91c of the wireless microphone 91 and thereby the frequency characteristic, the gain and so on of the sound signal of the wireless microphone 91 are controlled.

In a case where plural performers respectively carry wireless microphones, the operator carrying the PDA 99 is able to control functions of the respective wireless microphones of the performers. The use of the PDA 99 advantageously makes it easy to control the functions.

As described previously, the infrared interface 91c of the wireless microphone 91 and the infrared interface 11c of the receiver 11 have a two-way communication function. In this embodiment, since the infrared interface 99c of the PDA 99 has a two-way communication function, two-way communication is able to be made between the wireless microphone 91 and the PDA 99. Therefore, by sending the reply information from the wireless microphone 91 to the PDA 99, the PDA 99 is informed that the wireless microphone 91 has received the infrared signal from the PDA 99 or the wireless microphone 91 has been controlled correctly according to the information from the PDA 99.

Alternatively, communication may be performed between the receiver 11 and the PDA 99. With this configuration, the information of the setting conditions of the transmitter 91b may be sent from the receiver 11 to the PDA 99, and further from the PDA 99 to wireless microphone 91 (transmitter). To be specific, first, the receiver 11 performs infrared communication with the PDA 99 as if the receiver 11 performed infrared communication with the transmitter 91b of the wireless microphone 91. Thereby, the command information or the attribute information is output from the receiver 11 to the PDA 99, which stores these information in the internal storage portion. Then, the PDA 99 sends the information stored in the storage portion to the transmitter 91b of the wireless microphone 91. The wireless microphone 91 changes the setting conditions or stores the received attribute information in the internal storage portion as if the wireless microphone 91 received these information from the receiver 11.

When the receiver 11 sends to the PDA 99, reply request information to request the PDA 99 to inform the receiver 11 of the setting conditions of the wireless microphone 91, the PDA 99 sends to the receiver 11, the information regarding the setting conditions of the wireless microphone 91 that is stored in the internal storage portion, as reply information.

When the PDA 99 sends the reply request information to the transmitter 91b of the wireless microphone 91, the transmitter 91b of the wireless microphone 91 sends the reply information to the PDA 99, in response to the reply request information. Based on the reply information, the PDA 99 is able to recognize the setting conditions of the wireless microphone 91, for example, the gain of the sound signal of the wireless microphone 91. Based on this information, the PDA 99 may send to a transmitter of another wireless microphone, for example, command information to change the setting conditions of the transmitter of another wireless microphone.

In a further alternative, the information regarding the wireless microphone may be communicated between two PDAs by infrared communication. In other words, one of the two PDAs acts as the transmitter of the wireless microphone and the other acts as the receiver. Thereby, information regarding the wireless microphone is communicated between the two PDAs.

As described previously, when the information of all setting conditions regarding one transmitter are sent to the receiver 11, another transmitter is able to change the setting conditions into those identical to the setting conditions of the one transmitter. In the configuration in which communication is performed between the receiver 11 and the PDA 99, one transmitter and another transmitter are configured to have the same setting conditions by an operation performed as follows. First, the receiver 11 sends to the corresponding transmitter (first transmitter), reply request information regarding the setting conditions of the transmitter. The transmitter (first transmitter) sends to the receiver 11, the information regarding the setting conditions. Then, the receiver 11 communicates the information of the setting conditions of the transmitter (first transmitter) to the PDA 99. Then, the PDA sends command information to another transmitter (second transmitter) so that the setting conditions of the transmitter (second transmitter) become identical to those of the transmitter (first transmitter).

By using a dedicated remote controller or a general-purpose remote controller as the PDA, the wireless microphone communication system becomes inexpensive.

Figure 12:
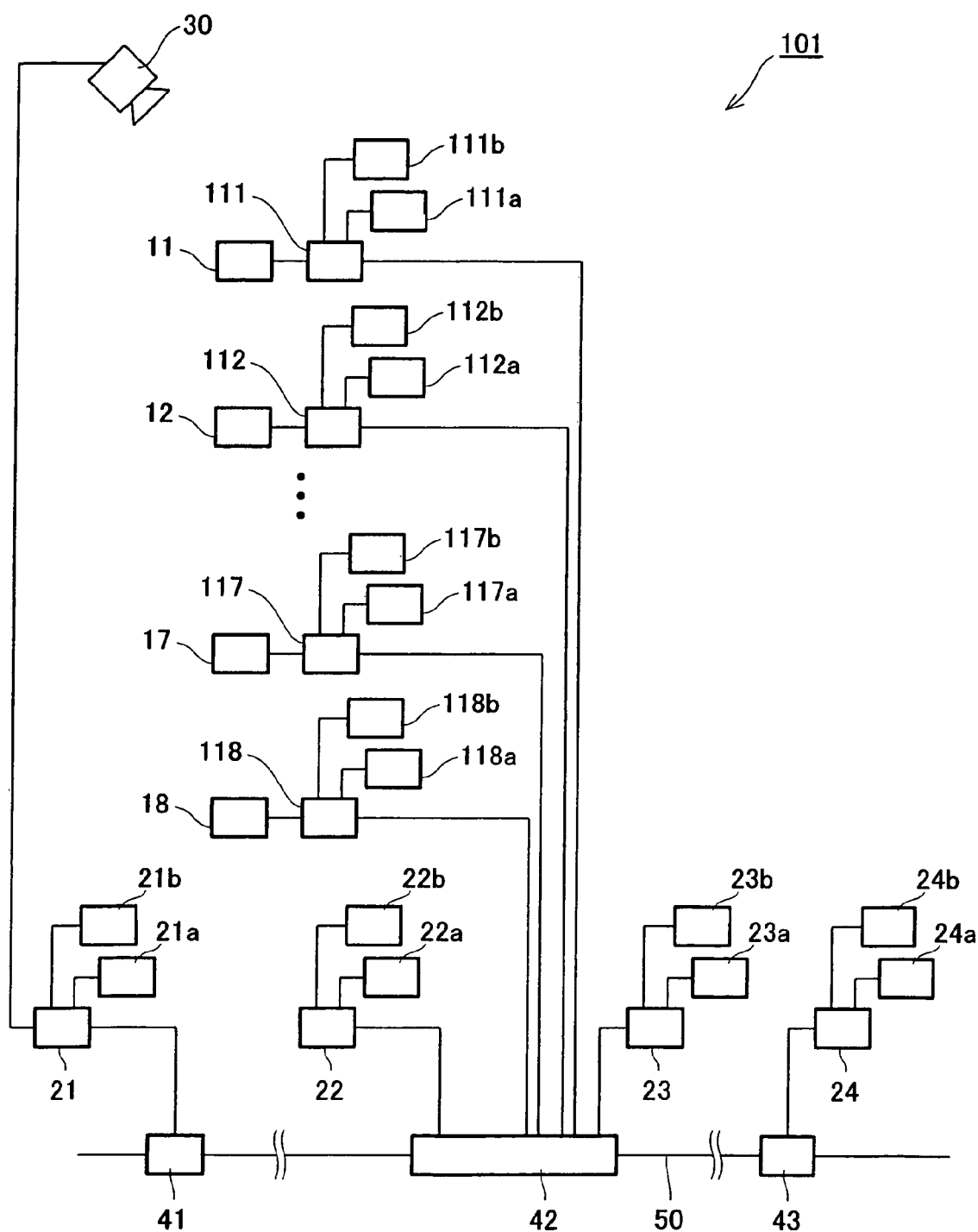
FIG. 12 is a block diagram of a wireless microphone communication system.

Subsequently, a wireless microphone communication system in which receivers that receive radio waves from transmitters of wireless microphones are coupled to LAN through controllers having LAN interfaces will be described. FIG. 12 is a view schematically showing a configuration of a wireless microphone communication system 101.

The wireless microphone communication system 101 includes the computers 21, 22, 23, and 24 as in the wireless microphone communication system 1 of FIG. 1. The computers 21, 22, 23, and 24 in FIG. 12 have functions identical to those of the computers 21, 22, 23, and 24 of FIG. 1.

The wireless microphone communication system 101 is different from the wireless microphone communication system 1 of FIG. 1 as follows. In the wireless microphone communication system 1 of FIG. 1, the receivers 11 to 18 have the LAN interfaces and are coupled to the HUB 42 through the LAN interfaces rather than the controllers 21 to 24, while in the wireless microphone communication system 101 in FIG. 12, the receivers 11 to 18 are coupled to the HUB 42 through the controllers 111 to 118 having the LAN interfaces. The controllers 111 to 118 may be configured by computers.

As in the computers 21 to 24, key boards 111a to 118a which are input devices and display devices 111b to 118b are coupled to the controllers 111 to 118.

Each of the controllers 111 to 118 receives information from another controller to which the corresponding receiver is coupled. The information from the controller includes, the RF level (receiving field intensity), the audio output level (VU level), and so on. The wireless microphone corresponding to each receiver sends, to the receiver, information of the battery power of the wireless microphone. Each of the controllers 111 to 118 receives the information of the battery power from another controller. These information are displayed on the display devices 111b to 118b. That is, the respective controllers 111 to 118 have functions identical to those of the computers 21 to 24.

The controllers 111 to 118 in the wireless microphone communication system 101 of FIG. 12 are operated by an operator.

The controllers 111 to 118 in the wireless microphone communication system 101 of FIG. 12 enable plural operators to equally recognize the state of the communication system using the wireless microphones.

Subsequently, another wireless microphone communication system in which the receivers that receive the radio wave from the transmitters of wireless microphones are coupled to the LAN through the controllers having the LAN interfaces will be described.

FIG. 12 shows the wireless microphone communication system 101 in which the controllers 111 to 118 to which the receivers 11 to 18 that receive the radio wave from the transmitters of the wireless microphones are coupled, through the LANs, to the controllers 21, 22, 23, and 24 to which the receivers are not coupled.

The controllers (computers) 21, 22, 23, and 24 to which the receivers are not coupled and the corresponding peripheral devices 21a, 21b, 22a, 22b, 23a, 23b, 24a, and 24b may be omitted from the wireless microphone communication system 101 of FIG. 12. This results in a wireless microphone communication system in which the plurality of (eight) controllers (computers) 111 to 118 to which the receivers 11 to 18 that receive the radio wave from the transmitters of the wireless microphones are coupled to each other through the LAN. While eight controllers (computers) 111 to 118 are coupled to the common HUB 42 in FIG. 12, the respective controllers (computers) 111 to 118 may alternatively be equipped with HUBs which are coupled to the Ethernet 50. In a case where the plurality of controllers (computers) 111 to 118 are installed to be distant from each other, they may be operated by the associated operators. These operators are able to equally recognize the state of the communication system using the wireless microphones.

Numerous modifications and alternative embodiments of the invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention and all modifications which come within the scope of the appended claims are reserved.

INDUSTRIAL APPLICABILITY

In accordance with the present invention, functions of a wireless microphone are controlled by an external infrared signal. Therefore, the present invention is applicable to fields of wireless microphone communication systems.

The invention claimed is:

1. A wireless microphone communication system comprising:
   a wireless microphone including a sound receiving portion and a transmitter; and
   a receiver for receiving a sound signal transmitted from the wireless microphone through a radio wave, characterized in that
   the wireless microphone communication system further comprises a portable information communication device including a storage portion;
   each of the transmitter, the receiver, and the portable information communication device has an infrared interface;
   the receiver transmits to the portable information communication device through the infrared interface at least one piece of information selected from the group consisting of: command information for commanding control of a function of the wireless microphone, request information for requesting the receiver to notify a setting state of the wireless microphone, and information regarding a type of a battery used in the transmitter of the wireless microphone;
   the portable information communication device stores in the storage portion the at least one piece of information received from the receiver through the infrared interface and transmits to the transmitter through the infrared interface the at least one piece of information stored in the storage portion; and
   the transmitter receives the at least one information from the portable communication device through the infrared interface.

2. The wireless microphone communication system according to claim 1, wherein the at least one piece of information is the command information, and the transmitter controls the function of the wireless microphone based on the command information.

3. The wireless microphone communication system according to claim 2, wherein the command information is information regarding an amplitude frequency characteristic of a sound signal, and the command information is to command the transmitter of the wireless microphone to control the amplitude frequency characteristic of the sound signal.

4. The wireless microphone communication system according to claim 2, wherein the command information is information regarding a gain of a sound signal, and the command information is to command the transmitter of the wireless microphone to control a gain given to the sound signal.

5. The wireless microphone communication system according to claim 2, wherein the command information is information regarding a frequency of a carrier wave, and the command information is to command the transmitter of the wireless microphone to control the frequency of the carrier wave.

6. The wireless microphone communication system according to claim 2, wherein the command information is information regarding an output level of a carrier wave, and the command information is to command the transmitter of the wireless microphone to control the output level of the carrier wave.

7. The wireless microphone communication system according to claim 2, wherein the command information is information regarding whether or not to permit a setting condition of the transmitter to be changed, and the command information is to command the transmitter of the wireless microphone to enable or disable an operation portion of the transmitter of the wireless microphone to change the setting condition.

8. The wireless microphone communication system according to claim 2, wherein the command information is information regarding deviation, and the command information is to command the transmitter of the wireless microphone to control the deviation.

9. The wireless microphone communication system according to claim 2, wherein the command information is information regarding a pilot tone, and the command information is to command the transmitter of the wireless microphone to start or stop transmission of the pilot tone.

10. The wireless microphone communication system according to claim 2, wherein the command information is information regarding a display, and the command information is to command the transmitter of the wireless microphone to cause the display into an operating state or a non-operating state.

11. The wireless microphone communication system according to claim 2, wherein the command information is information regarding a compander, and the command information is to command the transmitter of the wireless microphone to control a characteristic of the compander.

12. The wireless microphone communication system according to claim 2, wherein the command information is information regarding a mute function, and the command information is to command the transmitter of the wireless microphone to cause the mute function into an operating state or a non-operating state.

* * * * *